US005738998A

United States Patent [19]
Deth

[11] Patent Number: 5,738,998
[45] Date of Patent: Apr. 14, 1998

[54] COMPOSITIONS AND METHODS FOR DIAGNOSING SCHIZOPHRENIA

[76] Inventor: Richard C. Deth, 1484 Beacon St., Waban, Mass. 02168

[21] Appl. No.: 449,651

[22] Filed: May 24, 1995

[51] Int. Cl.$^6$ .................................................. G01N 33/53
[52] U.S. Cl. .................... 435/7.21; 436/518; 436/519; 436/161; 436/174; 436/811
[58] Field of Search ................................ 435/7.1, 7.21, 435/7.92, 7.95, 960; 436/518, 519, 530, 531, 63, 86, 89, 161, 174, 175, 811; 424/9.1, 9.2

[56] References Cited

FOREIGN PATENT DOCUMENTS

WO90/05780   5/1990   WIPO.
WO96/06856   3/1996   WIPO.

OTHER PUBLICATIONS

Roberts et al., Schizophrenia Research, 20(1–2): 171–174, 1996.
Smythies et al., "Abnormalities of One–Carbon Metabolism in Psychiatric Disorders: Study of Methionine Adenosyltransferase ...", Chemical Abstracts, vol. 106, No. 5, issued Feb. 2, 1987, p. 363, No. 30903w.
Tolbert et al., "Defects in Transmethylation and Membrane Lipids in Schizophrenia", Chemical Abstracts, vol. 100, No. 1, issued Jan. 2, 1984, p. 378, No. 4318r.
Kelsoe Jr. et al., "Kinetic Evidence for Decreased Methionine Adenosyltransferase Activity in Erythrocytes from Schizophrenia", Chemical Abstracts, vol. 98, No. 5, issued Jan. 31, 1983, p. 491, No. 32472v.
"Schizophrenia and Other Psychotic Disorders," In Diagnostic and Statistical Manual of Mental Disorders, (Washington, D.C.: American Psychiatric Association) Fourth Edition, pp. 273–296.
Taubes, G., "Will New Dopamine Receptors Offer a Key to Schizophrenia?" Science, 265:1034–1035 (1994).
Teeter, M.M. et al., "Homology Modeling of the Dopamine $D_2$ Receptor and Its Testing by Docking of Agonists and Tricyclic Antagonists," J. Med. Chem., 37(18):2874–2888 (1994).
Van Tol, H.H.M. et al., "Cloning of the Gene for a Human Dopamine $D_4$ Receptor With High Affinity for the Antipsychotic Clozapine," Nature 350:610–614 (1991).
Samama, P. et al., "A Mutation–Induced Activated State of the $\beta_2$–Adrenergic Receptor," J. Biol. Chem., 268(7):4625–4636 (1993).
Ismail, L. et al., "Altered Metabolism of the Methionine Methyl Group in the Leukocytes of Patients with Schizophrenia," Society of Biological Psychiatry pp. 649–660 (1978).
Kelsoe, J.R. et al., "Kinetic Evidence for Decreased Methionine Adenosyltransferase Activity in Erythrocytes from Schizophrenics," J. Neuroscience Research, 8:99–103 (1982).
Sargent, T. III et al., "Tracer Kinetic Evidence for Abnormal Methyl Metabolism in Schizophrenia," Biol. Psychiatry, 32:1078–1090 (1992).

Kemali, D. et al., "Antidepressant Effects of Adenosyl–Methionine: Clinical and Methodological Issues Emerging from Preliminary Trials," In Biochemical and Pharmacological Roles of Adenosylmethionine and the Central Nervous System, Zappia et al., eds. (NY: Pergamon Press), pp. 141–147 (1978).
Trolin, C.G. et al., "Brain ATP:L–Methionine S–Adenosyltransferase (MAT), S–Adenosylmethionine (SAM) and S–Adenosylhomocysteine (SAH): Regional Distribution and Age–Related Changes," European Neuropsychopharmacology, 4:469–477 (1994).
O'Dowd, B.F., "Structures of Dopamine Receptors," J. Neurochemistry, 60(3):804–816 (1993).
Seeman, P. et al., "Brain Receptors for Antipsychotic Drugs and Dopamine: Direct Binding Assays," Proc. Nat. Acad. Sci. USA, 72(11):4376–4380 (1975).
Seeman, P. and Van Tol, H.H.M., "Dopamine Receptor Pharmacology," In TiPs Receptor and Ion Channel Nomenclature Supplement, S. Watson and D. Girdlestone, eds., 5th edition (1994).
Hilf, G. and Jakobs, K.H., "Activation of Cardiac G–Proteins by Muscarinic Acetylcholine Receptors: Regulation by $Mg^{2+}$ and $Na^+$ ions," European J. Pharmacology, 172:155–163 (1989).
"Antibody Detection and Preparation," In Current Protocols in Immunology, J.E. Coligan et al., (John Wiley & Sons, Inc.) National Institutes of Health, pp. 2.0.1–2.5.17 (1994).
Seeman, P. et al., "Dopamine D4 Receptors Elevated in Schizophrenia," Nature, 365:441–445 (1993).
Tolbert, L.C. et al., "Defects in Transmethylation and Membrane Lipids in Schizophrenia," Psychopharmacology Bulletin, 19(4):594–599 (1983).
Le Fur, G. et al., "Evidence for a Coupling Between Dopaminergic Receptors and Phospholipid Methylation in Mouse B Lymphocytes, Life Sciences, 29:2737–2749 (1981).
Mezey, É. and Palkovits, M., "Localization of Targets for Anti–Ulcer Drugs in Cells of the Immune System," Science, 258:1662–1665 (1992).
Szymanski, S. et al., "A Selective Review of Biological Markers in Schizophrenia," Schizophrenia Bulletin, 17(1):99–111 (1991).
Macciardi, F. et al., "Analysis of the $D_4$ Dopamine Receptor Gene Variant in an Italian Schizophrenia Kindred," Arch. Gen. Psychiatry, 51:288–294 (1994).

(List continued on next page.)

Primary Examiner—Paula K. Hutzell
Assistant Examiner—Patricia A. Duffy
Attorney, Agent, or Firm—Hamilton, Brook, Smith & Reynolds, P.C.

[57] ABSTRACT

Methods and compositions for detecting schizophrenia based on modification of the dopamine $D_4$ receptor by addition of an adenosyl group to methionine #313 via methionine adenosyltransferase are described herein. Individuals with schizophrenia have a deficiency in methionine adenosyltransferase activity and a lower amount of modified dopamine $D_4$ receptor than normal individuals. Methods for screening therapeutic processes, agents and drugs for use in treatment of schizophrenia are also described.

4 Claims, 6 Drawing Sheets

OTHER PUBLICATIONS

Israelstam, D.M. et al., "Abnormal Methionine Metabolism in Schizophrenic and Depressive States: a Preliminary Report." *J. Psychiat. Res.*, 7:185–190 (1970).

Hilbert, M.F. et al., "Three–Dimensional Models of Neurotransmitter G–Binding Protein–Coupled Receptors." *Molecular Pharmacology*, 40:8–15 (1991).

Smythies, J.R. et al., "Abnormalities of One–Carbon Metabolism in Psychiatric Disorders: Study of Methionine Adenosyltransferase Kinetics and Lipid Composition of Erythrocyte Membranes." *Biol. Psychiatry*, 21:1391–1398 (1986).

De La Rosa, J. et al., "Changes in the Relative Amount of Subunits of Methionine Adenosyltransferase in Human Lymphocytes upon Stimulation with a Polyclonal T Cells Mitogen." *J. Biol. Chem.*, 267(15):10699–10704 (1992).

Hoffman, J.L., "Fractionation of Methionine Adenosyltransferase Isozymos (Rat Liver)." *Methods in Enzymology*, 94:223–247 (1983).

Baldessarini, R.J. et al., "Methylation in Schizophrenia: An Old Hypothesis Revisited." pp. 127–140 (1978).

Chou, T–C. et al., "The Enzymatic Synthesis of Adenosylmethionine: Mechanism and Inhibition." In *The Biochemistry of Adenosylmethionine*, (NY: Columbia University Press) pp. 18–36 (1977).

Iversen, L. L., "The D4 and Schizophrenia." *Nature*, 365:393 (1993).

FIG. IA
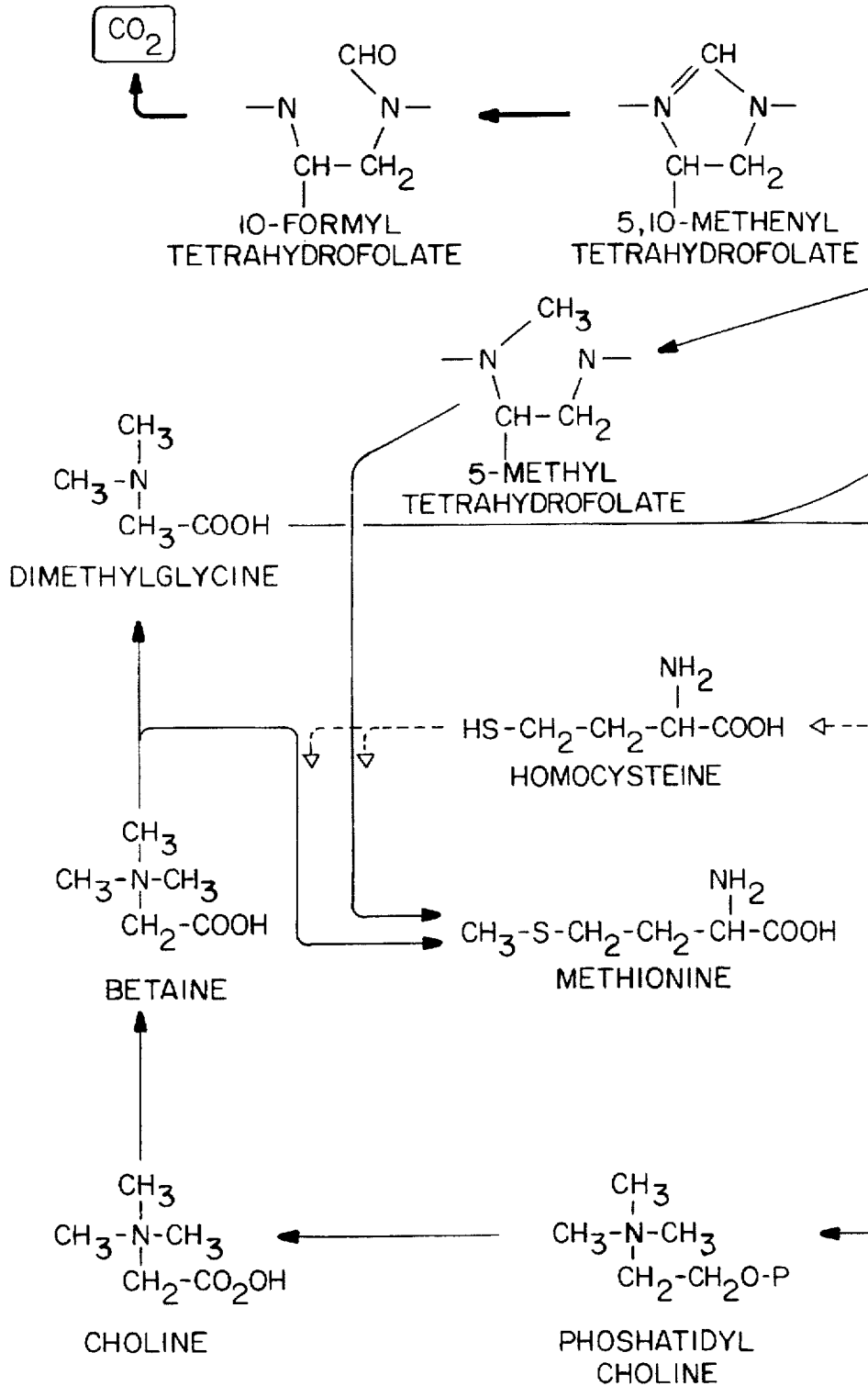

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 387 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

| | | | | | | | | | | | | | | | |
|---|---|---|---|---|---|---|---|---|---|---|---|---|---|---|---|
| Met | Gly | Asn | Arg | Ser | Thr | Ala | Asp | Ala | Asp | Gly | Leu | Leu | Ala | Gly | Arg |
| 1 | | | | 5 | | | | | 10 | | | | | 15 | |
| Gly | Pro | Ala | Ala | Gly | Ala | Ser | Ala | Gly | Ala | Ser | Ala | Gly | Leu | Ala | Gly |
| | | | 20 | | | | | 25 | | | | | 30 | | |
| Gln | Gly | Ala | Ala | Ala | Leu | Val | Gly | Gly | Val | Leu | Leu | Ile | Gly | Ala | Val |
| | | 35 | | | | | 40 | | | | | 45 | | | |
| Leu | Ala | Gly | Asn | Ser | Leu | Val | Cys | Val | Ser | Val | Ala | Thr | Glu | Arg | Ala |
| | 50 | | | | | 55 | | | | | 60 | | | | |
| Leu | Gln | Thr | Pro | Thr | Asn | Ser | Phe | Ile | Met | Ser | Leu | Ala | Ala | Ala | Asp |
| 65 | | | | | 70 | | | | | 75 | | | | | 80 |
| Leu | Leu | Leu | Ala | Leu | Leu | Val | Leu | Pro | Leu | Phe | Val | Tyr | Ser | Glu | Val |
| | | | | 85 | | | | | 90 | | | | | 95 | |
| Gln | Gly | Gly | Ala | Trp | Leu | Leu | Ser | Pro | Arg | Leu | Cys | Asp | Ala | Leu | Met |
| | | | 100 | | | | | 105 | | | | | 110 | | |
| Ala | Met | Asp | Val | Ala | Leu | Cys | Thr | Ala | Ser | Ile | Phe | Asn | Leu | Cys | Ala |
| | | 115 | | | | | 120 | | | | | 125 | | | |
| Ile | Ser | Val | Asp | Arg | Phe | Val | Ala | Val | Ala | Val | Pro | Leu | Arg | Tyr | Asn |
| | 130 | | | | | 135 | | | | | 140 | | | | |
| Arg | Gln | Gly | Gly | Ser | Arg | Arg | Gln | Leu | Leu | Leu | Ile | Gly | Ala | Thr | Trp |

-continued

| | | | | | | | | | | | | | | | |
|---|---|---|---|---|---|---|---|---|---|---|---|---|---|---|---|
| 145 | | | | | 150 | | | | | 155 | | | | | 160 |
| Leu | Leu | Ser | Ala | Ala 165 | Val | Ala | Ala | Pro | Val 170 | Leu | Cys | Gly | Leu | Asn 175 | Asp |
| Val | Arg | Gly | Arg 180 | Asp | Pro | Ala | Val | Cys 185 | Arg | Leu | Glu | Asp | Arg 190 | Asp | Tyr |
| Val | Val | Tyr 195 | Ser | Ser | Val | Cys | Ser 200 | Phe | Phe | Leu | Pro | Cys 205 | Pro | Leu | Met |
| Leu | Leu 210 | Leu | Tyr | Trp | Ala | Thr 215 | Phe | Arg | Gly | Leu | Gln 220 | Arg | Trp | Glu | Val |
| Ala 225 | Arg | Arg | Ala | Lys | Leu 230 | His | Gly | Arg | Ala | Pro 235 | Arg | Arg | Pro | Ser | Gly 240 |
| Pro | Gly | Pro | Pro | Ser 245 | Pro | Thr | Pro | Pro | Ala 250 | Pro | Arg | Leu | Pro | Gln 255 | Asp |
| Pro | Cys | Gly | Pro 260 | Asp | Cys | Ala | Pro | Pro 265 | Ala | Pro | Gly | Leu | Pro 270 | Pro | Asp |
| Pro | Cys | Gly 275 | Ser | Asn | Cys | Ala | Pro 280 | Pro | Asp | Ala | Val | Arg 285 | Ala | Ala | Ala |
| Leu | Pro 290 | Pro | Gln | Thr | Pro | Pro 295 | Gln | Thr | Arg | Arg | Arg 300 | Arg | Arg | Ala | Lys |
| Ile 305 | Thr | Gly | Arg | Glu | Arg 310 | Lys | Ala | Met | Arg | Val 315 | Leu | Pro | Val | Val | Val 320 |
| Gly | Ala | Phe | Leu | Leu 325 | Cys | Trp | Thr | Pro | Phe 330 | Phe | Val | Val | His | Ile 335 | Thr |
| Gln | Ala | Leu | Cys 340 | Pro | Ala | Cys | Ser | Val 345 | Pro | Pro | Arg | Leu | Val 350 | Ser | Ala |
| Val | Thr | Trp 355 | Leu | Gly | Tyr | Val | Asn 360 | Ser | Ala | Leu | Asn | Pro 365 | Val | Ile | Tyr |
| Thr | Val 370 | Phe | Asn | Ala | Glu | Phe 375 | Arg | Asn | Val | Phe | Arg 380 | Lys | Ala | Leu | Arg |
| Ala 385 | Cys | Cys | | | | | | | | | | | | | |

COMPOSITIONS AND METHODS FOR DIAGNOSING SCHIZOPHRENIA

BACKGROUND

Schizophrenia is a devastating neuropsychiatric disorder which affects approximately 1% of the population and results in serious disruption in the lives of afflicted individuals and their families. Common symptoms include delusions, conceptual disorganization and visual or auditory hallucinations, as well as changes in affective behavior. A number of scales for the rating of symptoms and methods for ascertaining the diagnosis have been developed, including the DSM classification by the American Psychiatric Association (Diagnostic and Statistical Manual of Mental Disorders (4th edition), pp. 273–316 (1994)), which have attempted to refine the accuracy of clinical diagnosis. However, it is likely that similar symptoms can result from several underlying abnormalities, and diagnosis relying solely on clinical symptoms is difficult and controversial, as well as subjective, time-consuming and costly.

The cause or causes of schizophrenia remain obscure. A defect in dopamine pathways of synaptic neuronal function is a central feature of the most widely held etiopathogenic theory (known as the Dopamine Hypothesis), with recent emphasis on the role of $D_4$-type dopamine receptors (Taubes, Science 265:1034–1035 (1994)). However, studies to date have failed to identify abnormalities in the basic receptor structure, suggesting that dysfunction may result from an alteration in the dynamic regulation of receptor activity.

Dopamine receptors are members of a large superfamily of G protein-coupled receptors which share a high degree of structural similarity while recognizing a widely divergent array of substances which affect cellular function. Recent advances in the study of these receptors, including the development of 3-dimensional structural models (Teeter, et al., J. Med Chem 37:2874–2888 (1994)), have led to the identification of key locations on the receptors which can modulate their function and which therefore may be sites of malfunction in schizophrenia (Samama et al., J. Biol. Chem. 268:4625–4636 (1993)). One such critical location or "hot spot" in the dopamine $D_4$ receptor is a methionine amino acid residue (Van Tol et al., Nature 350:610–614 (1991)).

A number of clinical and metabolic studies have documented altered methionine metabolism in individuals with schizophrenia (Kelsoe et al., J. Neurosci. Res. 8:99–103 (1982), Ismail et al., Biol. Psych. 13:649–660 (1978), Sargent et al., Biol. Psych. 32:1078–1090 (1992)). Conversely, administration of S-adenosylmethionine has been shown to have antidepressant benefits (Kemali et al., Biochemical and Pharmacological Roles of Adenosylmethionine and the Central Nervous System, Pergamon Press, pp. 141–147 (1979)). Despite the evidence for the importance of an abnormality of methionine metabolism, a cogent hypothesis relating these observations to schizophrenia has not emerged. Until now it has not been possible to integrate findings of altered methionine metabolism with the central role of dopamine receptor function, an integration which would provide an entirely new approach to the diagnosis and treatment of schizophrenia. A reliable biochemical assay would not only provide a more rapid and facile basis for diagnosis, but would also ease the continuing stigma associated with the disease by providing a clearly definable chemical cause for a disease which is presently considered a "mental disorder".

SUMMARY OF THE INVENTION

This invention is based upon the discovery that a biochemical abnormality in methionine metabolism associated with schizophrenia is linked to the clinical manifestations of altered dopamine neurotransmission. This discovery provides novel and empirical approaches for the diagnosis and treatment of schizophrenia.

This invention pertains to novel biochemical methods for diagnosing schizophrenia and other neuropsychiatric disorders, including schizo-affective disorders and dementias. The method of the present invention is based on the fact that dopamine receptor function is abnormal in individuals with schizophrenia, and upon the discovery, described herein, that methionine residue #313 (human $D_4$ receptor numbering) of the dopamine $D_4$ receptor is abnormally modified in schizophrenic individuals. Methionine residue #313 is normally modified by the addition of an adenosyl group to its sulfur atom via the action of a methionine adenosyltransferase (MAT) enzyme; however, individuals with schizophrenia are deficient in MAT activity and, thus, possess a lesser amount of the modified dopamine $D_4$ receptor. This deficiency is evident in a variety of tissues, including brain tissue and blood cells, particularly white blood cells, and is central to the biochemical diagnosis of schizophrenia.

In one embodiment of the present invention, the level of MAT or MAT activity in a tissue sample from an individual to be tested is measured using standard methods such as measuring the formation of [$^3$H]S-adenosylmethionine from [$^3$H]methionine as described in Trolin et al., Eur. Neuropsych 4:469–477 (1994). The measured level is then compared with the corresponding level from a tissue sample of a normal individual; a lower level of MAT or MAT activity in the tested individual compared with the normal individual is indicative of schizophrenia in the tested individual.

According to another embodiment of the present invention, antibodies which specifically recognize either the modified form of the receptor or the unmodified form of the dopamine D4 receptor are produced by methods described herein. Such antibodies are also the subject of the present invention. The antibodies are used alone or in combination to assess the extent of $D_4$ receptor modification, and can be used in preparations of white blood cells, white blood cell membranes or platelets or other cell types which contain the $D_4$ receptor. The level of binding of antibodies which specifically recognize the unmodified receptor region which includes methionine #313 will be higher in schizophrenic individuals than in normal individuals. Reciprocally, the level of binding of antibodies which specifically recognize the modified receptor will be significantly lower in schizophrenic individuals than in normal individuals.

In order to normalize the level of binding to the total amount of D4 receptor present in the tissue, the binding of the specific antibodies can be expressed relative to the binding of an antibody which binds to a region of the D4 receptor which does not undergo modification; that is, the latter antibody recognizes both the modified and unmodified form of the receptor (Ab-BOTH).

In an alternate embodiment of the invention, the determination of the amount of modified and unmodified receptors can be made by isolation of the receptor protein itself, followed by chemical analysis of individual amino acids or peptide fragments which contain the site of methionine modification. For instance, proteolytic enzymes or chemicals could be used to cleave the $D_4$ receptor into peptide fragments or individual amino acids. The presence of a modified methionine residue could be detected using spectral analysis, chromatography or other standard means for determining the occurrence of a modified amino acid. The occurrence of modified methionine residues is lower in schizophrenic individuals than in normal individuals.

Alternatively, modification of an isolated receptor could be assayed using the receptor as a substrate for the MAT enzyme, and measuring the extent of further adenosylation using, for example, the incorporation of radioactive adenosine triphosphate. In this case, the receptors from schizophrenic individuals would show a higher rate of modification than those from normal individuals, as they have a lower level of modification as a baseline.

As described herein, the methods of the present invention can be used to distinguish between modified and unmodified receptors, particularly modified and unmodified dopamine $D_4$ receptors. The present methods can also be used to determine, by standard procedures, relative levels of modified and unmodified receptors. Thus, the compositions and methods of the present invention have utility for diagnosis of schizophrenia, as well as for assessment of progression of the disease and assessment of the effectiveness of treatment programs for schizophrenia and other neuropsychiatric disorders by monitoring levels of modified and unmodified receptors and/or levels of enzyme, or enzyme activity particularly MAT or MAT activity.

This invention also pertains to novel methods for identifying therapeutic processes, agents or drugs for treatment of schizophrenia. Processes, agents and drugs identified by the methods described herein can increase the amount of MAT enzyme or MAT enzyme activity. For example, the process, agent or drug can mimic the effect of methionine adenosyltransferase in adding an adenosyl group to methionine #313. Alternatively, the process, agent or drug can increase the ability of the $D_4$ receptor to become adenosylated, possibly by increasing the ability of the receptor to achieve the active conformation from which it can be adenosylated. This can also be achieved by a partial agonist or antagonist. Alternatively, effective therapeutic processes, agents or drugs can decrease the deadenosylation of S-adenosylmethionine. For example, the process, agent or drug can inhibit the effect of the putative phospholipid methyltransferase, adenosylhomocysteine hydrolase or methionine synthetase enzymes which convert modified methionine receptors to unmodified methionine receptors. This can be achieved by introducing a substrate which competes with the adenosylated methionine for the action of the putative adenosylase. Preferably this competitive substrate is not metabolized to methionine.

This invention also pertains to novel methods for determining the effectiveness of therapeutic processes and agents for treatment of schizophrenia. In one embodiment of the invention, the effectiveness of a therapeutic process or agent can be assessed by making an initial determination of the amounts of modified and unmodified $D_4$ receptors in a tissue sample from an individual to be tested, administering the process or agent to be assessed, and making a subsequent determination of amounts of modified and unmodified $D_4$ receptors in the tissue sample from the individual. The corresponding levels of modified and unmodified receptors can be compared; an increase in the amount of modified receptor and/or a decrease in the amount of unmodified receptor indicates that the process or agent is effective for treating schizophrenia.

In a particular embodiment, the determination of the amounts of modified and unmodified receptors is carried out using two types of antibodies, one of which specifically recognizes the modified form of the receptor and the other of which specifically recognizes the unmodified form of the receptor. The results can optionally be normalized to the total amount of $D_4$ receptor present by expressing the binding of the specific antibodies relative to the binding of an antibody which recognizes both the modified and unmodified forms of the receptor (Ab-BOTH).

In an alternate embodiment, the effectiveness of a therapeutic process or agent can be assessed by making an initial determination of the level of MAT or MAT activity in a tissue sample from an individual to be tested, administering the process or agent to be assessed, and making a subsequent determination of the level of MAT or MAT activity in a tissue sample from the individual. An increase in the MAT level or MAT activity level indicates that the process or agent is effective in treating schizophrenia. Thus, the present invention has utility for the identification of agents, processes and drugs for use in the treatment of schizophrenia, and such agents, processes and drugs are also the subject of this invention.

BRIEF DESCRIPTION OF THE DRAWINGS

FIGS. 1A and 1B are a schematic illustration of the major pathways for the metabolism of free methionine.

FIG. 5A illustrates the ability of cycloleucine, a methionine adenosyltransferase (MAT) inhibitor, to inhibit spontaneous G protein binding of [$^{35}$S]GTPγS in Chinese hamster ovary cells which express the cloned dopamine $D_4$ receptor. FIG. 5B shows the inability of cycloleucine to affect spontaneous [$^{35}$S]GTPγS binding in Chinese hamster ovary cells without the $D_4$ receptor.

DETAILED DESCRIPTION OF THE INVENTION

Figure 2:
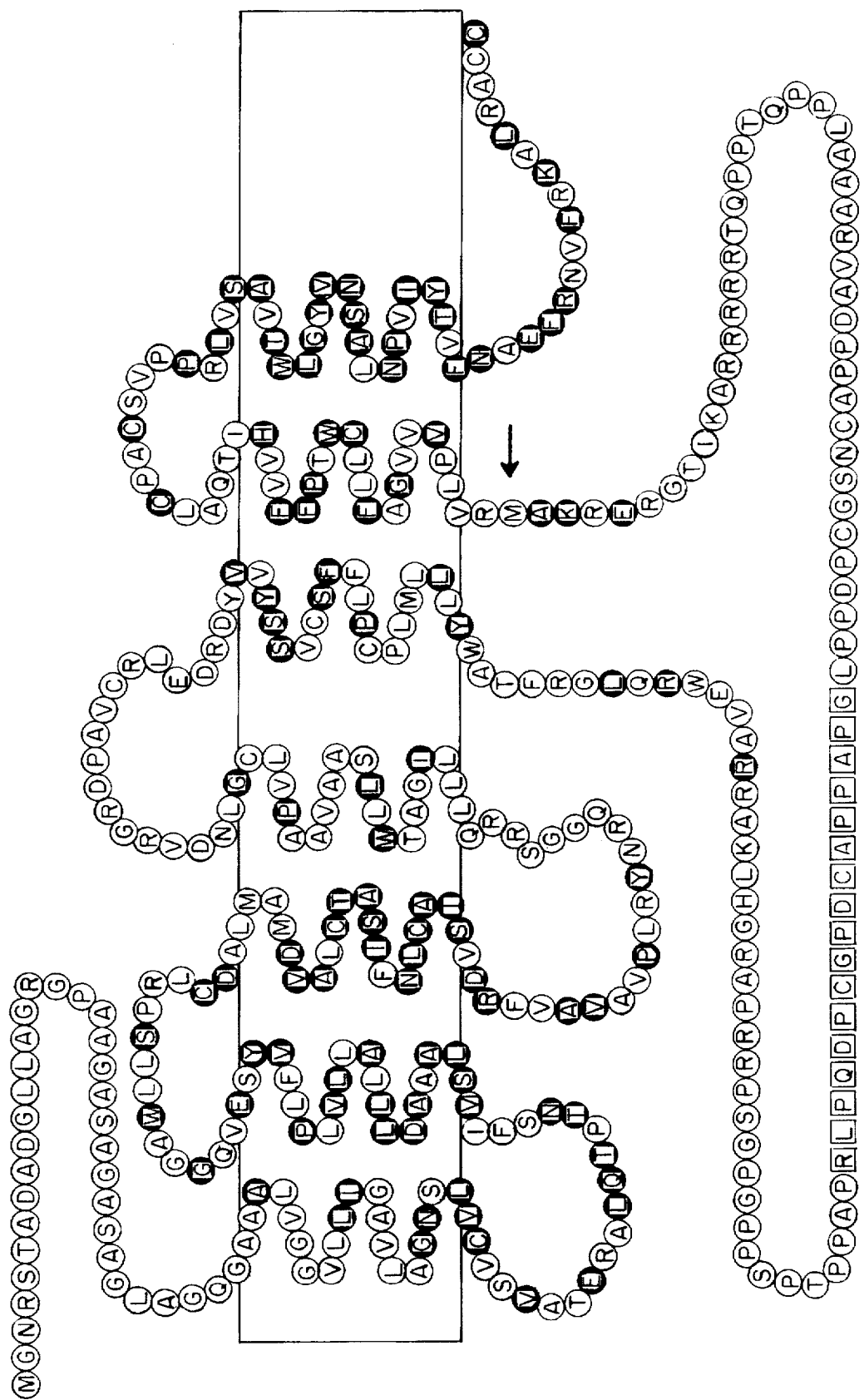
FIGS. 2 illustrates the dopamine $D_4$ receptor structure and shows the amino acid sequence (SEQ ID NO: 1) of the human dopamine $D_4$ receptor and its proposed seven transmembrane helical elements. The cell membrane is shown as a rectangle with the extracellular surface at the top and intracellular surface at the bottom. Methionine #313 (the "hot spot") is indicated with an arrow.

The "Dopamine Hypothesis" is the most widely held biochemical explanation for the etiology of schizophrenia and theorizes a defect in dopamine pathways of synaptic neuronal function, with recent emphasis on the role of $D_4$-type dopamine receptors. Dopamine receptors are members of the superfamily of G protein-coupled receptors. All G protein-coupled receptors share the basic structural motif of seven transmembrane-spanning helices, formed as the single polypeptide chain traverses the plasma membrane (Figure 2, O'Dowd, *J. Neurochem* 60:804–816 (1993)). In the case of the dopamine receptor, the neurotransmitter dopamine diffuses into the central core of the receptor on the outer surface of the cell where critical amino acid residues provide specific recognition. The binding of dopamine and its recognition by the receptor cause an alteration in the conformation of the receptor, and this "active" conformation conveys the neurotransmitter signal to GTP-binding G proteins located on the inner surface of the cell membrane.

Five subtypes of dopamine receptors have been identified, designated as $D_1$, $D_2$, $D_3$, $D_4$ and $D_5$. Based upon functional and structural similarities, the $D_1$ and $D_5$ receptors form a $D_1$-like receptor group, and the $D_2$, $D_3$ and $D_4$ receptors comprise a $D_2$-like group. Among dopamine receptors, the $D_1$-like receptors primarily complex with and activate the G protein $G_s$, while the $D_2$-like receptors activate the $G_i$ and/or $G_o$ proteins. The potency of neuroleptic drugs in treating schizophrenia has been found to be closely correlated with their antagonism of the $D_2$-like receptors (Seeman et al., Proc. Nat. Acad. Sci. USA 72:4376-4380 (1975)), and antagonism of the $D_4$ receptor subtype provides a better correlation than do the $D_2$ or $D_3$ subtypes, implicating the $D_4$ receptor as the most likely target of neuroleptic drugs (Seeman and Van Tol, Trends Pharmacol Sci 15:264-270 (1994)).

Generally, a receptor must be occupied by its agonist or partial agonist in order to attain its active conformation and convey the neurotransmitter signal. However, in a phenomenon known as "receptor precoupling", it is possible for a receptor to maintain the active conformation even in the absence of agonist occupation, although the extent of this phenomenon appears to be dependent upon prior exposure of the cells to the appropriate agonist.

Figure 4:
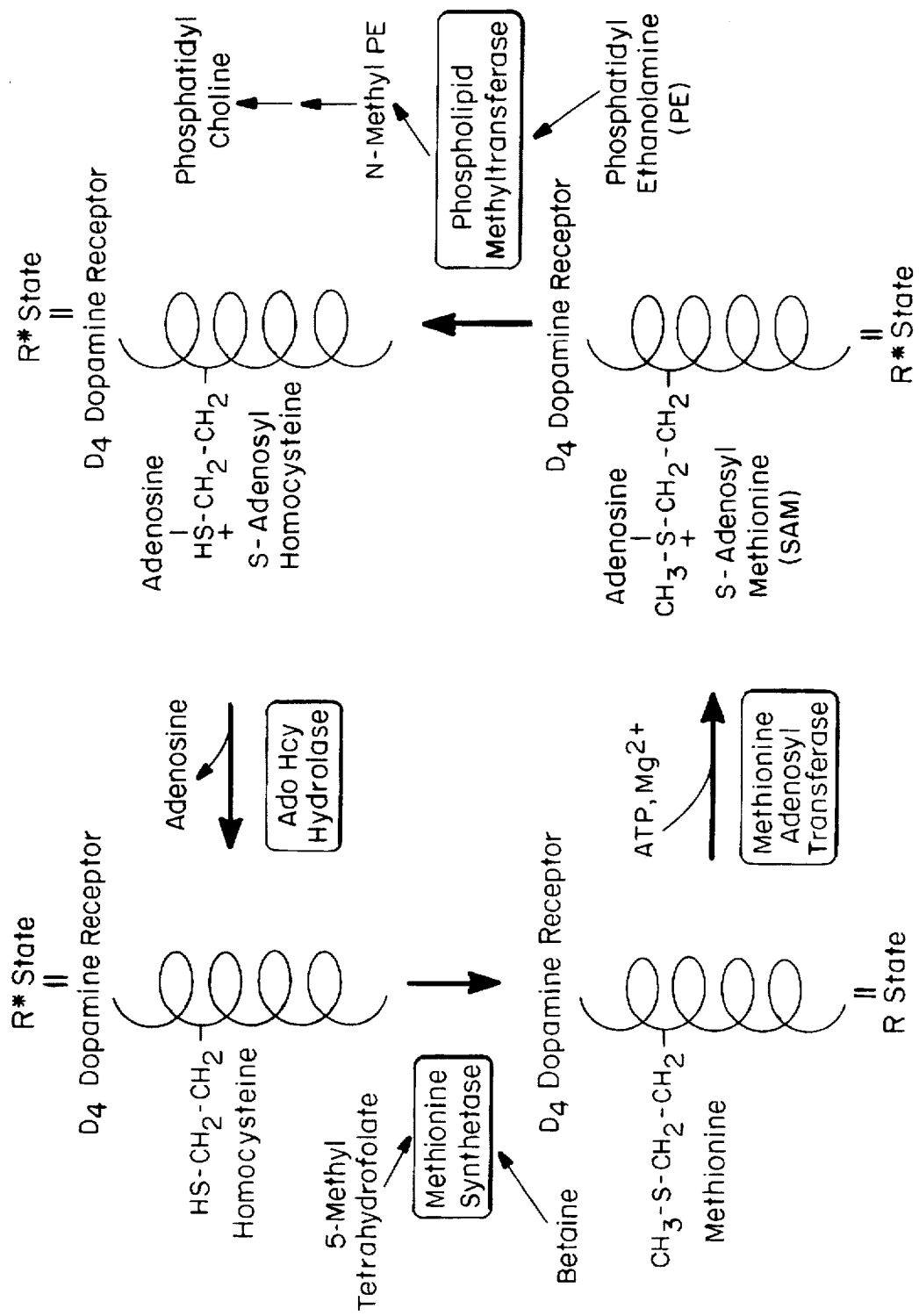
FIG. 4 illustrates the cyclical conversion of the $D_4$ receptor from its unmodified methionine form ($D_4$(MET)) to its modified (adenosylated) form ($D_4$(SAM)), to two additional modified forms ($D_4$(AdoHCY) and $D_4$(HCY)), and finally back to its unmodified form. This cyclic pathway mimics the metabolism of free methionine shown in FIG. 1. The modified forms of the receptor ($D_4$(SAM), $D_4$(AdoHCY) and $D_4$(HCY)) are spontaneously active.

Without wishing to be bound by theory, the binding of the agonist apparently induces a conformational change in the receptor, causing it to become active. In this active state, a modifiable amino acid residue (a "hot spot") on the intracellular portion of the receptor, exactly 18 residues (5 helical turns) from the agonist binding site, becomes accessible to a native enzyme. This enzyme modifies the "hot spot" such that the modification (typically a phosphorylation in other precoupled receptors but adenosylation in the $D_4$ receptor) prevents the receptor from returning to the inactive conformation upon departure of the agonist. In fact, the receptor remains in the active conformation, and continues to propagate the neurotransmitter signal, until the modification is removed by subsequent enzyme activity (FIG. 4).

As a result of work described herein, the dopamine $D_4$ receptor, methionine #313 (human $D_4$ receptor numbering) has been identified as such a "hot spot"; that is, methionine #313 is a modifiable amino acid residue on the intracellular portion of the $D_4$ receptor, located 18 residues (exactly 5 helical turns) below the key residue which is utilized by agonists to induce the active receptor conformation. It has been shown that any modification of residues occupying the same position as dopamine $D_4$ receptor methionine #313 in other receptors will cause the receptor to become spontaneously active and exhibit precoupling (Samama et al., J. Biol Chem 268:4625-4636 (1993)).

Figure 1B:
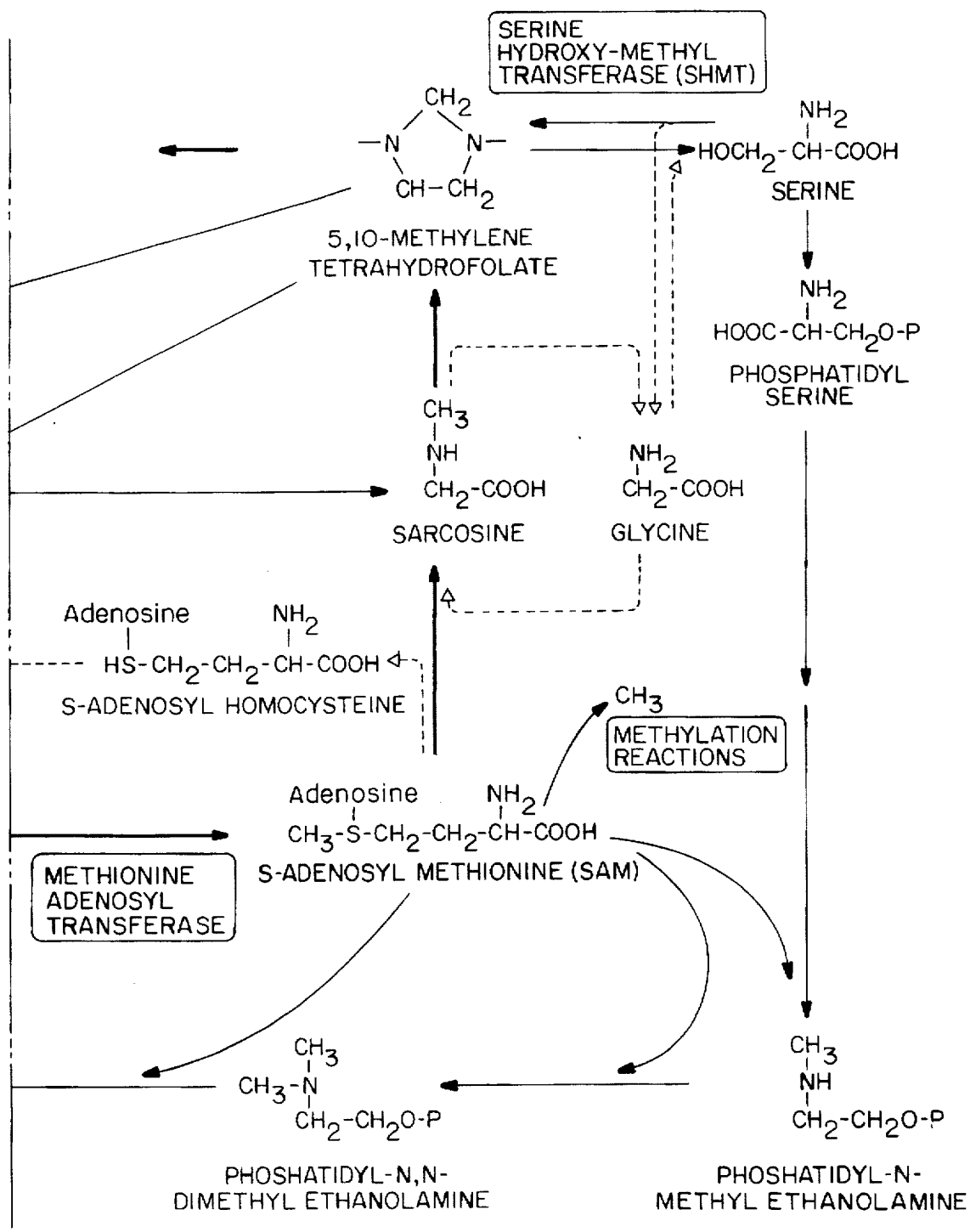

A number of clinical and metabolic studies have documented altered methionine metabolism in individuals with schizophrenia (Kelsoe et al., J. Neurosci Res 8:99-103 (1982), Ismail et al., Biol Psych 13:649-660 (1978), Sargent et al., Biol Psych 32:1078-1090 (1992)). Conversely, administration of S-adenosylmethionine has been shown to have antidepressant benefits (Kemali et al., Biochemical and Pharmacological Roles of Adenosylmethionine and the Central Nervous System, Pergamon Press, pp. 141-147 (1979)). The major metabolic pathways for free methionine are illustrated in FIG. 1. The conversion of methionine to S-adenosylmethionine is a key step in methionine metabolism, and a methionine adenosyltransferase (MAT) enzyme participates in this conversion.

It is believed that the binding of dopamine to the $D_4$ receptor causes an alteration of the receptor conformation to the active conformation. As a result of this alteration, methionine #313 (human $D_4$ receptor numbering) becomes accessible to MAT, and MAT adds an adenosyl group to the sulfur atom of the methionine. This modification of methionine #313 by MAT prevents the re-configuration of the receptor to the inactive form upon departure of the agonist. Thus, the dopamine $D_4$ receptor is capable of spontaneously maintaining its active conformation, i.e., maintaining its active conformation without dopamine occupation (FIG. 4). This active conformation is maintained until the modification (e.g., the adenosyl group) is removed by subsequent enzyme activity. A deficiency in MAT enzyme activity could account for the observed decrease in methionine utilization in schizophrenics.

A number of other neurotransmitter receptors can also be modified, particularly by phosphorylation, at a site which is equivalent to methionine #313, and it is possible that abnormal levels of receptor modification are associated with other psychiatric disorders or disease states. The methods described herein can be used to determine abnormalities in modification of receptors other than the dopamine $D_4$ receptor.

For instance, the $\alpha_2$-adrenergic receptor, $M_2$- and $M_4$-muscarinic receptors, $D_2$- and $D_3$-dopaminergic receptors, $\mu$- and $\delta$-opiate receptors, $SS_2$- and $SS_3$-somatostatin receptors and $5$-$HT_{1B}$, $5$-$HT_{1D}$ and $5$-$HT_{2C}$ receptors all possess a modifiable amino acid residue on the intracellular portion of the membrane; exactly 18 amino acid residues (5 helical turns) separate the modifiable amino acid from the amino acid residue which is the agonist binding site on the extracellular portion of the receptor. A modifiable amino acid residue located at this position is considered a "hot spot", and modification of residues at this "hot spot" position of the receptor cause the receptor to become spontaneously active and exhibit precoupling (Samama et al., J. Biol Chem 268:4625-4636 (1993)). Usually a modifiable amino acid is a serine residue or a threonine residue which can be modified by phosphorylation; however, as the present invention shows, other residues such as methionine can be modified.

Thus, the methods described herein can be used to diagnose and monitor neuropsychiatric disorders, in addition to schizophrenia, which result from abnormal receptor modification. Specifically, after the "hot spot" modifiable amino acid residue in the receptor of interest, and/or the enzyme or enzymes responsible for the modification are identified, the levels of modified, or unmodified receptor or enzyme activity can be determined and compared with normal levels. A difference in the levels of modified receptor, unmodified receptor and/or enzyme activity compared with normal levels is indicative of abnormality in receptor modification and resultant neuropsychiatric disorder.

Figure 5A:
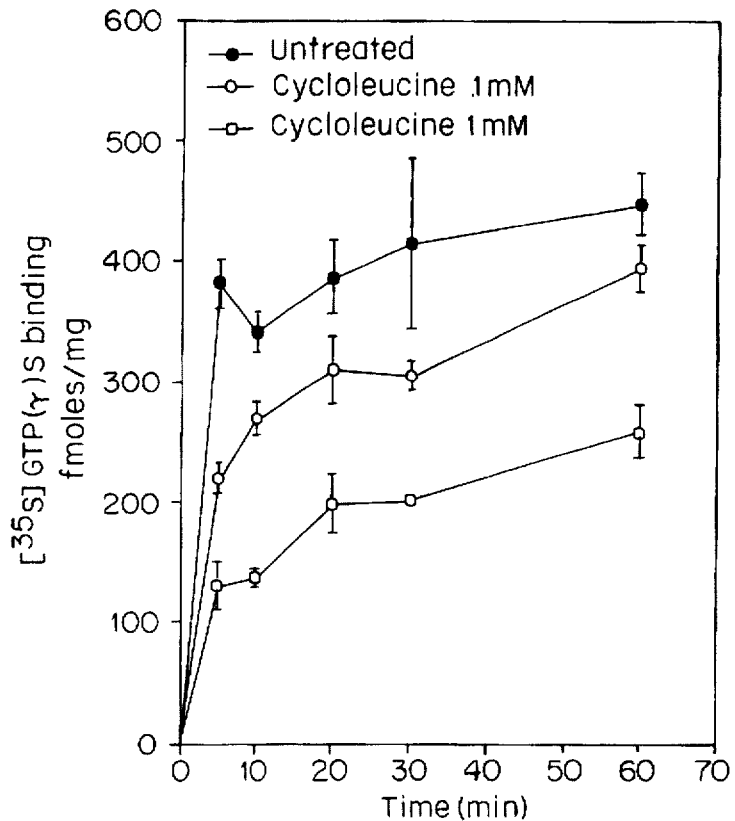
FIGS. 5A and 5B illustrate graphic representations of the effect of cycloleucine on spontaneous G protein binding of [$^{35}$S]GTPγS.
Figure 5B:
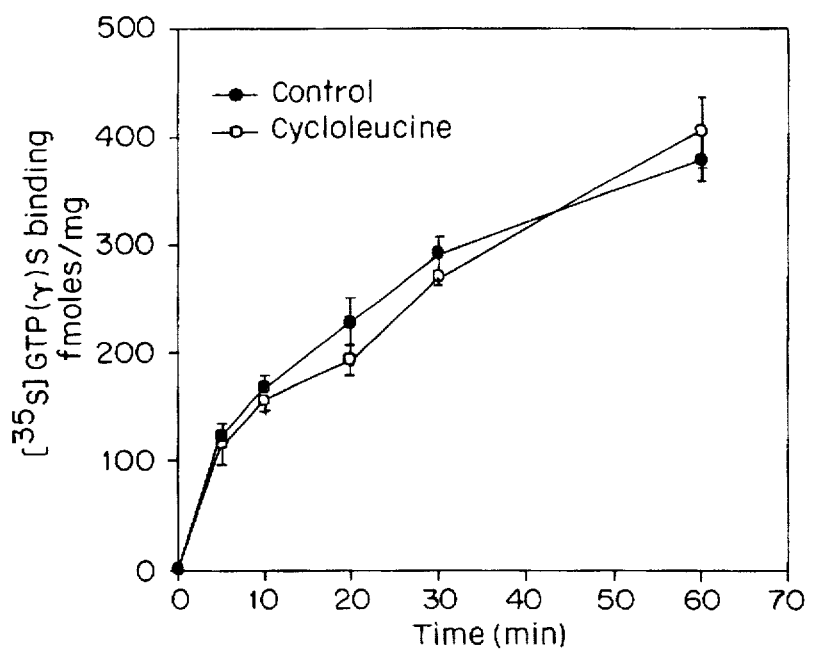

The degree of spontaneous activity of the receptor can be monitored by measuring the level of G protein activation, and particularly by measuring the binding of [$^{35}$S]GTPγS. The effect of cycloleucine, a known MAT inhibitor, on the binding of [$^{35}$S]GTPγS was tested by treating Chinese hamster ovary cells expressing the $D_4$ receptor with 0.1 mM and 1 mM cycloleucine prior to membrane preparation (FIG. 5A). The binding of [$^{35}$S]GTPγS to the membranes was progressively reduced by 0.1 mM and 1 mM cycloleucine pretreatment to levels significantly lower than the untreated control membranes. Thus, inhibition of MAT, such as with cycloleucine, results in a decrease in G protein activation, confirming that MAT is a key factor in spontaneous activity of the dopamine $D_4$ receptor.

The present invention relates to methods for determining the level of MAT or MAT activity. One method involves a direct determination of the level of MAT enzyme or MAT enzyme activity in a tissue sample. This determination can be carried out using standard techniques for assaying enzyme presence or activity.

An alternative method involves a determination of the levels of $D_4$ receptor which have been modified to include an adenosyl group on methionine #313, and those which have not been modified. The modified receptor can be in the form of S-adenosyl methionine ($D_4$(SAM)), S-adenosyl homocysteine ($D_4$(AdoHCY)) or homocysteine ($D_4$(HCY)), since (as shown in FIG. 4) a deficiency in MAT activity results in lower levels of all three forms. The determination of modified receptor level can be carried out using standard techniques. Methionine modification serves as an indicator of MAT activity because the modification process requires MAT activity to proceed. Thus, a high level of modified receptor and correspondingly low level of unmodified receptor correlates to a high level of MAT activity, while a low level of modification and reciprocal high level of unmodified receptor is consistent with a low level of MAT activity.

The methods described herein are useful in diagnosing schizophrenia and other neuropsychiatric disorders. While one enzyme of interest in schizophrenia is MAT, the enzyme or enzymes of interest in other neuropsychiatric disorders can be protein kinases (e.g., protein kinase A or protein kinase C) or protein phosphatases. The particular enzymes assayed will depend upon the particular modification of the "hot spot" residue.

According to the present invention, the level of MAT or MAT activity in a tissue sample from an individual to be tested is measured, and this level is compared with the corresponding level of MAT or MAT activity in a tissue sample from a normal individual. If the MAT or MAT activity level of the tissue sample from the tested individual is less than that of the normal tissue sample, the results are indicative of schizophrenia. If the MAT activity level of the tissue sample from the tested individual is equal to or greater than that of the normal tissue sample, the results are not indicative of schizophrenia.

Similarly, the levels of modified and/or unmodified $D_4$ receptor in a tissue sample from an individual to be tested can be measured, and these levels can be compared with the corresponding levels in a tissue sample from a normal individual. If the level of modified receptor is greater in the normal tissue sample than in the tested sample, and/or the level of unmodified receptor is lower in the normal tissue sample than in the tested sample, this is consistent with a reduced level of MAT activity in the tested sample, and indicative of schizophrenia.

Regardless of which of the above approaches are used, the determination of MAT activity is carried out by testing a tissue sample from an individual of interest. Any tissues which display the schizophrenia-associated alterations in methionine metabolism are suitable for use in the present invention. Such tissues include brain tissue and red and white blood cells. White blood cells, white blood cell membranes and platelets are particularly useful in the present invention because of their accessibility, allowing the methods of the present invention to be carried out on a blood sample from the individual.

Antibodies designed to specifically recognize either the modified or unmodified form of the receptor are particularly useful for measuring the level of modified $D_4$ receptor in a tissue sample from an individual. Such antibodies can be used to determine the level of receptor modification by measuring the amount of binding of antibodies which specifically recognize the adenosylated methionine #313 in $D_4$(SAM), $D_4$(AdoHCY) and/or $D_4$(HCY); the determination and quantification of antibody binding can be carried out using standard techniques, such as Western blotting, ELISA and fluorescence-activated cell scanning (FACS) assays.

Figure 3:
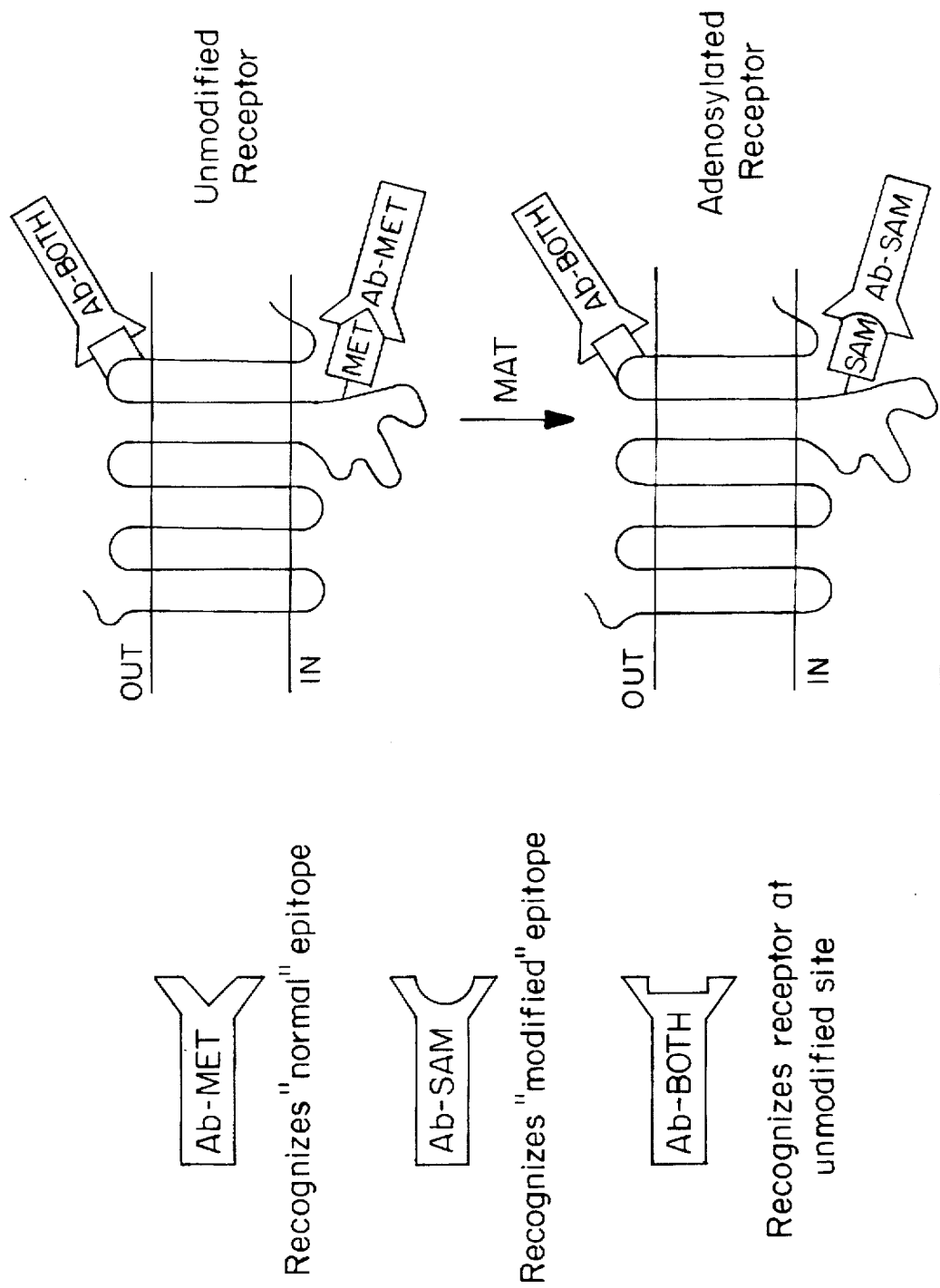
FIG. 3 illustrates a schematic diagram of antibody-based determination of receptor modification using Ab-MET Ab-SAM, and Ab-BOTH as examples.

According to one embodiment of the invention, peptides corresponding to the unmodified receptor region of interest, e.g., the dopamine $D_4$ receptor region containing unmodified methionine #313, are synthesized and conjugated to an immunogenic hapten. Various immunogenic haptens are known in the art, and those of particular utility include keyhole limpet hemocyanin (KLH) and bovine serum albumin (BSA). Antibodies are raised against the conjugate which selectively recognize only receptors containing the unmodified methionine (Ab-MET, FIG. 3). Standard techniques, such as those described in *Current Protocols in Immunology* (Vol. I, Wiley Interscience (1994)), can be used to construct the antibodies of the present invention.

Peptides corresponding to the modified receptor region of interest, e.g., the dopamine $D_4$ receptor region containing methionine #313 which has been modified by addition of an adenosyl group to its sulfur atom in the $D_4$(SAM), $D_4$(AdoHCY) and/or $D_4$(HCY) forms, can also be synthesized and conjugated to an immunogenic hapten. Antibodies are raised against these conjugates which recognize only the receptor containing the modified methionine. For instance, antibodies can be raised against $D_4$(SAM) which recognize only the S-adenosyl methionine (SAM) form of the $D_4$ receptor (Ab-SAM, FIG. 3). Based upon the metabolism of methionine itself, three distinct modified forms of the $D_4$ receptor can be identified, as shown in FIG. 4. Since reduced activity of the initial modifying enzyme (MAT) is thought to be the primary defect in schizophrenia, quantitation of the percentage of unmodified $D_4$ receptors to all modified forms of the receptor is a particularly useful diagnostic determination.

An antibody (e.g., Ab-BOTH) which recognizes the $D_4$ receptor without regard to its state of modification (e.g., at an extracellular loop) is useful for detection of the entire $D_4$ receptor population and for identifying those cells which contain $D_4$ receptors and those which do not.

The synthetic peptide which is conjugated to an immunogenic hapten and used to raise antibodies should be long enough to provide unique recognition of the target receptor region to the exclusion of other receptors or regions thereof. Thus, the appropriate length of the peptide will vary depending upon the target receptor region; however, generally the length of the peptide is from about 6 amino acids to about 15 amino acids. Additional amino acid residues can also be added to the peptide to facilitate coupling of the peptide to the hapten or to enhance the immunogenicity of the peptide. Alternatively, the unmodified methionine residue itself can be used to raise an antibody which specifically recognizes only this residue.

In order to determine the relative levels or ratio of modified to unmodified receptors in a given sample, and thus determine the existence of a deficiency or excess in MAT activity, each of the specific antibodies can be coupled to a different detection system. For instance, rabbit Ab-MET could be detected using goat anti-rabbit IgG coupled to horseradish peroxidase, while mouse Ab-SAM could be detected using goat anti-mouse IgG coupled to alkaline phosphatase. The ratio of peroxidase to phosphatase activity in a sample under standard conditions provides an estimate of the predominance of the unmodified form of the receptor versus the modified form of the receptor.

The amount of modified or unmodified receptor present in a sample can also be directly compared with the amount of corresponding modified or unmodified receptor in a sample from a normal individual. The levels of modified and unmodified receptors in the normal sample can be determined concurrently with the determination in the tested sample, or the normal determination can be made in advance and used as a baseline level total compare future samples against. A higher level of unmodified receptor and/or a lower level of modified receptor in the tested individual compared with normal levels is indicative of schizophrenia.

The following Examples are offered for the purpose of illustrating the present invention and are not to be construed to limit the scope of the present invention:

EXAMPLES

Assay for Binding of GTP to G Proteins

Chinese hamster ovary (CHO) cells stably expressing a cloned dopamine $D_4$ receptor were grown as monolayers at 37° (95% $O_2$/5%$CO_2$) in alpha minimum essential medium supplemented with 2.5% fetal calf serum, 2.5% horse serum, 100 units/ml penicillin, 100 µg/ml streptomycin, 0.25 µg/ml fungizone and 400µg/ml G418.

Cells were washed twice with phosphate-buffered saline (137 mM NaCl, 2.6 mM KCl, 10 mM $Na_2HPO_4$, 1.8 mM $KH_2PO_4$), harvested with a rubber policeman, and pelleted at 4° at 200×g. The pellet was resuspended in 5 ml/dish of lysis buffer (5 mM Tris.HCL, pH 7.5, 5 mM EDTA, 5 mM EGTA, 0.1 mM phenylmethylsulfonyl fluoride) at 4° and was homogenized with a Dounce homogenizer. The cell lysate was then centrifuged at 34,000×g for 15 minutes, and the pellet was resuspended in membrane buffer (50 mM Tris.HCl, pH 7.5, 0.6 mM EDTA, 5 mM $MgCl_2$, 0.1 mM phenylmethylsulfonyl fluoride) on ice. Aliquots were rapidly frozen in liquid nitrogen and stored at −80° until used.

[$^{35}$S]GTPγS binding was measured with a modification of the assay used by Hilf and Jakobs (*Eur J Pharmacol* 172:155–163 (1989)). Cell membranes were thawed and diluted with 10 mM Tris.HCl buffer. Membrane protein (4–8 µg) was mixed with reaction mixture (50 mM Tris.HCl, pH 7.5, 5 mM $MgCl_2$, unless otherwise specified, 1 mM EDTA, 1 mM dithiothreitol, 100 mM NaCl, 2 µM GDP and 2–3 nM [$^{35}$S]GTPγS, unless otherwise specified), in a total volume of 100 µl. The incubation was started by addition of reaction mixture to the membrane suspension and was carried out in at least triplicate for varying times at 25°. The reaction was terminated by rapid filtration through GF/C filters under vacuum. The filters were washed four times (with 4 ml of 50 mM Tris.HCl, pH 7.5, containing 5 mM $MgCl_2$ and 100 mM NaCl) and then counted in scintillation cocktail. Nonspecific binding was determined in the presence of 10 µM GTPγS and subtracted from total bound radioactivity.

Production of Antibodies

The amino acid sequence of the $D_4$ dopaminergic receptor was examined and compared with other receptors in order to identify the sequence which corresponds to the carboxyl terminus of the third intracellular loop. This sequence contained a methionine amino acid residue which can be structurally modified by methionine adenosyltransferase. For antibody production, a decapeptide containing the modified residue in an internal position, plus an added cysteine residue at the amino terminus for coupling purposes, was synthesized and purified by standard solid phase peptide synthesis techniques. The peptide was coupled (i.e., crosslinked with N-SIBA) via its cysteine residue to two different hapten proteins, bovine serum albumin (BSA) and keyhole limpet hemocyanin (KLH), to enhance its immunogenicity. The extent of conjugation was quantified by measuring the depletion of the reactive lysine residues in BSA and KLH using a TNBS assay. Additionally, the same peptide is prepared except that the modifiable residue is in its adenosylated, adenosylhomocysteine or homocysteine form, and this peptide is coupled to BSA and KLH.

Polyclonal Antibody Production

An initial pre-immune serum sample was obtained from each of two rabbits. The KLH-conjugated peptide was dissolved in water and mixed with an immunologic adjuvant (e.g., Complete Freund's adjuvant or TITERMAX®) to form an emulsion. An amount of emulsion containing 10–25 µg of the peptide was injected near each of the inguinal and axillary lymph nodes (i.e., four injection sites) of two rabbits for each peptide. Three weeks later a similar injection was given to boost the immunologic response, the booster injection was repeated six weeks after initial immunization. Blood samples were obtained approximately 10 days after each booster and analyzed by ELISA for the presence and titer of the desired antibodies, using the BSA-peptide conjugate as the source of antigen. Additional boosters can also be given at 3 week intervals until a desired titer (e.g., 1:50,000) is obtained.

While the crude polyclonal antiserum can be used for assay purposes, the active antibodies are preferably purified by standard affinity chromatography techniques to reduce background binding by non-specific antibodies. For this purpose the peptide is crosslinked to a column chromatography matrix (e.g., sepharose), and the antiserum passed through the column, allowing the specific antibodies to be retained by the column. Subsequently, the desired antibodies can be eluted from the column by washing it with buffer of higher ionic strength and pH.

It is also possible to use affinity column chromatography to deplete a serum sample of undesired antibody. For example, a column formed with the unmodified peptide could be used on a serum sample containing antibodies against the unmodified peptide to remove any antibodies whose binding is not strictly dependent upon the presence of the modification. ELISA assay of the eluates is used to monitor the effectiveness of depletion.

Monoclonal Antibody Production

For each peptide, 10 mice are immunized with the KLH-peptide conjugate along with adjuvant following the protocol outlined for polyclonal antibodies. When serum titers have reached the desired level, hybridomas are produced by fusing spleen cells (or other types of antibody-producing cells) from the immunized mice with murine myeloma cells (e.g., the Sp2/O-Ag14 cell line, using standard HAT (Hypoxanthine/Aminopterin/Thymidine) medium selection techniques. HAT-sensitive myeloma cells are grown in culture for 8 days and harvested. From 1 to 5×10$^7$ myeloma cells and 1 to 5×10$^6$ antibody-producing cells are mixed in Dulbecco's Modified Eagle's Medium in the presence of 30–50% polyethyleneglycol (molecular weight=100 to 5000) to promote cell fusion. Viruses can also be used to facilitate fusion. Cells are plated out and allowed to grow for 8 to 10 days in HAT medium. During this time only the hybridoma cells will survive, and such positive clones are expanded in culture wells and the supernatant from these wells is assayed for the presence of the desired antibody by ELISA, using the appropriate peptide as an antigen. Further cloning by dilution can yield a cell population producing a pure monoclonal antibody. Larger quantities of antibody are produced by injecting these cells into the peritoneal cavity of mice along with a mineral oil adjuvant. The ascites fluid which develops in 2 to 3 weeks contains high levels of the desired antibody.

Assay Methods for Measuring Receptor Modification

Once an antibody has been produced that will bind to the epitope region exclusively in its unmodified or modified form, the amount of its binding to a standard amount of receptor material defines the status of the modifiable residue. For instance, antibody which can bind only to the epitope region of the $D_4$ receptor in its non-adenosylated form can be used to detect the predominance of that form if the amount of antibody binding can be quantitated relative to the total amount of receptor material which is present in a given sample. The total amount of receptor material in a sample is quantitated by the binding of a second antibody to another region of the receptor which is not subject to modification, or with an antibody which binds both the modified and unmodified forms of the receptor equally well. This type of antibody can be considered to be "neutral antibodies" with regard to the modification status of the receptor. Thus, for a particular sample, the ratio of the specific antibody binding to the neutral antibody binding can be used as an index of the modification status. The binding of the antibodies can be detected and quantitated by a variety of standard techniques, including Western blots of proteins separated by gel electrophoresis, sandwich ELISA assays and fluorescence-activated cell sorting assays.

Equivalents

Those skilled in the art will recognize, or be able to ascertain using no more than routine experimentation, many equivalents to the specific embodiments of the invention described herein. Such equivalents are intended to be encompassed by the following claims:

What is claimed is:

1. An in vitro method of assessing the effectiveness of a therapeutic process or agent for treating schizophrenia in a patient, comprising the steps of:
   a) making an initial determination of the amount of dopamine D$_4$ receptors in a tissue sample from the patient which have and have not been modified by addition of an adenosyl group to methionine #313;
   b) administering to the patient the therapeutic process or agent to be assessed;
   c) making a subsequent determination in a sample of the same tissue type used in step (a) of the amount of dopamine D$_4$ receptors in the patient which have and have not been modified by addition of an adenosyl group to methionine #313; and
   d) comparing the corresponding amounts of modified and unmodified dopamine D$_4$ receptors from steps a) and c).

wherein an increase in the amount of modified receptors and/or a decrease in the amount of receptors which have not been modified subsequent to administration of the therapeutic process or agent indicates that the therapeutic process or agent is effective for treating schizophrenia in the patient.

2. A method according to claim 1 wherein the determination of the amount of dopamine D$_4$ receptors which have and have not been modified by addition of an adenosyl group to methionine #313 is carried out using antibodies.

3. A method according to claim 1, wherein steps b), c) and d) are carried out more than once.

4. A method of identifying therapeutic processes, agents and drugs useful for treating schizophrenia, comprising the steps of:
   a) making an initial determination of the amount of dopamine D$_4$ receptors which have been modified by addition of an adenosyl group to methionine #313 in a cell from a cell line which expresses the modified D$_4$ receptor;
   b) administering to the cell the therapeutic process, agent or drug to be tested;
   c) making a subsequent determination of the amount of dopamine D$_4$ receptors which have been modified by addition of an adenosyl group to methionine #313 in the cell; and
   d) comparing the corresponding amounts of modified receptors from steps a) and c).

wherein an increase in the amount of modified receptors subsequent to administration of the therapeutic process, agent or drug indicates that the therapeutic process, agent or drug is useful for treating schizophrenia.

* * * * *